(12) United States Patent
Polman (10) Patent No.: US 9,927,409 B2
(45) Date of Patent: Mar. 27, 2018

(54) METHOD AND DEVICE FOR INSPECTING CONTINUOUSLY FED OBJECTS

(71) Applicant: Eckhard Polman, Hunxe (DE)

(72) Inventor: Eckhard Polman, Hunxe (DE)

( * ) Notice: Subject to any disclaimer, the term of this patent is extended or adjusted under 35 U.S.C. 154(b) by 267 days.

(21) Appl. No.: 14/355,688

(22) PCT Filed: Nov. 5, 2012

(86) PCT No.: PCT/IB2012/002235
§ 371 (c)(1),
(2) Date: Jul. 30, 2014

(87) PCT Pub. No.: WO2013/064889
PCT Pub. Date: May 10, 2013

(65) Prior Publication Data
US 2014/0366658 A1     Dec. 18, 2014

(30) Foreign Application Priority Data
Nov. 4, 2011   (DE) .................... 20 2011 107 446 U (51) Int. Cl.
| G01N 33/00 | (2006.01) |
| G01M 3/32 | (2006.01) |
| G01M 3/36 | (2006.01) |
| G01M 3/34 | (2006.01) |

(52) U.S. Cl.
CPC .......... *G01N 33/00* (2013.01); *G01M 3/3218* (2013.01); *G01M 3/3281* (2013.01); *G01M 3/34* (2013.01); *G01M 3/363* (2013.01)

(58) Field of Classification Search
CPC .............................. G01N 33/00; G01M 3/363
USPC ......................................................... 73/865.8
See application file for complete search history.

(56) References Cited

U.S. PATENT DOCUMENTS 700,891 A   5/1902   Black
3,824,840 A   7/1974   Amberg

FOREIGN PATENT DOCUMENTS

| DE | 1573478 | 8/1970 |
| NL | 8900299 | 9/1990 |
| WO | WO 2010089101 A1 * | 8/2010 ............. B65G 17/46 |

OTHER PUBLICATIONS

International Bureau, (Translation of) International Search Report and Written Opinion for corresponding application PCT/IB2012/002235 (dated May 13, 2014).

* cited by examiner

*Primary Examiner* — Manish S Shah
*Assistant Examiner* — Jean Morello
(74) *Attorney, Agent, or Firm* — Fay Sharpe LLP (57) ABSTRACT

The invention relates to methods for inspecting objects fed in a continuous flow, in particular packages or components, wherein an inspecting body is guided along an inspection segment together with an object and a response to an inspection of the object is detected by means of a sensor in order to determine if the object meets a quality criterion, in particular is tight or leaky or true to size or functional.

41 Claims, 7 Drawing Sheets

METHOD AND DEVICE FOR INSPECTING CONTINUOUSLY FED OBJECTS

The present invention is a 371 National filing of PCT Application Serial No. PCT/IB2012/002235 filed Nov. 5, 2012, which in turn claims priority on German Patent Application Serial No. 20 2011 107 446.7 filed Nov. 4, 2011.

The invention relates to methods and devices for inspecting continuously fed objects which are fed in a continuous stream, in particular packagings or components.

The inspection of objects such as packagings and components with regard to quality criteria such as seal or dimensional accuracy is required in many technical fields. However, the known methods and devices are frequently complex, slow, susceptible to maintenance and discontinuous, as well as limited with regard to the inspection options. This is to be illustrated first of all using the seal inspection of packagings.

The seal inspection of packagings is required in many technical fields. For example, it has to be ensured in foodstuff packagings that the contents and a protective atmosphere which is possibly present cannot escape and the interior of the packaging is not contaminated by way of the penetration of foreign bodies or gases. Otherwise, the foodstuff becomes unenjoyable or the shelf life is shortened.

Packagings for other products than foodstuffs likewise have to be sealed, in order to avoid a loss of product as a result of leakage and contamination. Typical packages which have to be inspected for seal are beverage packages of all types, fresh meat packagings of all types, blister packagings, also for medicines, packed or welded foodstuff packagings, Tetra Paks, plastic beakers such as yoghurt beakers with a welded or adhesively bonded lid, beverage bottles, oil containers, ink containers, tubes, bottles and the like.

In the mass production of packaged products of this type, the object of inspecting every packaging and not merely samples for seal is to be achieved.

To this end, cyclical methods and devices for carrying out these methods are known, in which in each case a number of packagings are tested for seal together in an inspecting chamber. This is associated with a number of disadvantages, however. For instance, the packagings have to be arranged on a pallet and then moved into the inspecting chamber, pass through the inspection there, be removed from the inspecting chamber and subsequently be fed for further processing, for example labeling or the arrangement in packaging units. In mass production, packagings of this type are usually conveyed in a continuous stream, for example on a belt or the like, the belt being stopped briefly for filling and closing. This continuous packaging stream has to be interrupted, in order to collect a number of packagings on a pallet for seal inspection, and subsequently the packagings have to be transferred from the pallet into a packaging stream again for further processing. The results are a time delay and a considerable technical outlay. In addition, packagings which have been recognized to be leaky can be removed from the pallet only with highly technical outlay.

On account of the technical complexity, the known devices and packagings are expensive and susceptible to maintenance, and, during the transition from the continuous packaging stream to the cyclical inspection and then back into the continuous packaging stream, the risk of stoppages increases, since the packagings have to be rearranged mechanically multiple times.

The same disadvantages result during the inspection of objects in general, such as injection molded parts or else complex mechanical or electrical components, for example computer components, robot components, sensors, actuators, imagers, cameras, utensils, etc., which have to be subjected to a mechanical, electrical, thermal, magnetic, odor-based, vacuum-based and/or pressure-based and/or other stimulus such as switching on and off, taking of a photo, measurement of temperature, etc., in order to define a quality criterion and to separate faulty objects from fault-free objects.

Proceeding herefrom, the invention is based on the object of providing methods and devices for continuous inspection which are fed in a continuous stream, in particular packagings or components which make a 100% check possible without time loss in a manner which is rapid, inexpensive, failsafe in technical terms, and low-maintenance, that is to say reliable.

Accordingly, a method is provided for inspecting objects which are fed in a continuous stream, in particular packagings or components, in which an inspecting body is moved together with an object along an inspecting section and a reaction to an inspection of the object is detected by means of a sensor, in order to determine whether the object satisfies a quality criterion, in particular is sealed or leaky or dimensionally accurate or functional. In this way, rapid continuous inspection of objects can be realized.

The inspecting body preferably causes an inspection of the object. For example, the inspecting body can load the object with a vacuum, a pressure and/or a mechanical, acoustic, optical, thermal and/or electrical or other test pulse and/or can actuate, deflect, fill, empty, switch on and/or off, or stimulate in some other way the object or a part thereof.

The inspecting body can expediently comprise the sensor, in order to detect the reaction to a stimulation directly. For example, in the case of mechanical stimulation, for example deformation or actuation of the object by way of a mechanical test object, the pressure for the deformation or actuation can be measured directly, which can provide, for example, an indication of a leaky object which, as a result of the escape of enclosed gas, can be deformed more simply than a sealed object, in which the enclosed gas cannot escape. However, the sensor can also be arranged outside the inspecting body. It goes without saying that a plurality of, in particular different, sensors can be used.

An optical, acoustic, thermal, mechanical or other reaction of the object can be detected by means of the sensor and can be inspected with regard to a quality criterion.

In one embodiment, a method is provided for the vacuum-based seal inspection of packagings which are fed in a continuous packaging stream, in particular foodstuff packagings, in which method a sealing body is moved together with a packaging along an inspecting section and is loaded with vacuum and a reaction to the loading of the packaging with vacuum is detected by means of a sensor, in order to determine whether the packaging is sealed or leaky. As a result, the seal inspection can be integrated into the production process at any desired point, without influencing the production process. For example, the seal inspection can take place directly after filling and closing, while the packagings are fed in a continuous packaging stream to a further processing station, such as labeling. This results in a reduction in the technical complexity, and no packagings have to be removed from the packaging stream and inserted back into it after the seal inspection. A 100% inspection, that is to say an inspection of each individual packaging, is possible without time loss in a manner which is rapid, inexpensive, failsafe in technical terms and low-maintenance.

The continuous packaging stream is realized here, for example, by way of a conveyor belt or an endless conveyor.

Here, the packagings are moved in a transport direction so as to follow one another in one row or optionally with several packagings next to one another. The movement is continuous, that is to say flowing, the expression "continuous" for this application also comprising the change in the speed as far as a standstill, that is to say also quasi-continuous transport.

During the transport, the packagings pass through an inspecting section. There, a sealing body is moved together with the packagings. One sealing body is expediently provided for one packaging, but two or more packagings can be inspected at the same time by way of one sealing body which is then to be of correspondingly large configuration. The use of a multiplicity of sealing bodies which are moved together with the packagings along the inspecting section is expedient. A plurality of packagings can thus be subjected to a seal inspection at the same time.

A vacuum for inspecting the packagings is generated by way of the sealing bodies. As a reaction to the loading with vacuum, a deformation of the packaging, a pressure rise in the sealing body, a retarded vacuum formation in the sealing body, a gas in the sealing body and/or the like are/is detected.

If the deformation is detected, this takes place under the assumption that a leaky packaging does not inflate to such a pronounced extent as a sealed packaging, or remains completely non-deformed. This can be detected by way of an optical sensor, for example a digital camera with evaluation software. Optical sensors of this type are known in the inspection of products. Exceeding of a deformation limit can also be detected by way of an optical sensor of this type or simply by way of a light barrier which is interrupted in the case of sufficient deformation and thus signals a sealed packaging. Any desired optical sensors can be used for this purpose.

If the pressure rise in the sealing body or a retarded vacuum formation is detected, this takes place under the assumption that gas escapes from the leaky packaging and counteracts the vacuum formation. If the vacuum formation is retarded or delayed, this indicates a leak which was already in existence; for example, the packaging has been closed in a faulty manner or had mechanical defects. If the pressure suddenly rises, this indicates a leak which was produced under vacuum; for example, a weld or another closure or the packaging does not withstand the required mechanical loads. A diagnosis of the cause of the leak is therefore also possible. To this end, pressure sensors can be used, by way of which the actual pressure can be measured. A throughflow sensor can also be used, by way of which the quantity of extracted air can be detected; if gas is still flowing through the throughflow sensor after a defined time period, this indicates a leaky packaging. A pressure switch can also be used, in order to signal the seal if a defined vacuum is reached. A plurality of identical or different sensors can be combined.

Finally, a gas detector can be used, in order to detect gas in the sealing body, which gas should actually remain in the packaging, for example as protective gas, and can escape from said packaging only in the case of a leaky packaging. Since the gas which is contained in the packaging is known, an inexpensive gas detector which is adapted to said gas in a targeted manner can be used.

In order for it to be possible to generate a vacuum, the packaging is raised and/or the sealing body is lowered. To this end, corresponding mechanisms can be provided. The packagings are preferably arranged on a lower manifold, and the sealing body seals together with the lower manifold, the packaging or possibly a plurality of packagings at the same time being enclosed between the sealing body and the lower manifold. Here, the lower manifold can be a rubber plate of any desired shape, in particular round or polygonal, on which the packaging is situated. The lower manifold can also be a ring of any desired shape, in particular round or polygonal, in the interior of which the packaging is situated. The conveying device, on which the packagings are transported, is optionally made from a material, with respect to which the sealing bodies can seal, with the result that the conveying device forms the lower manifold.

Depending on the shape and closure of the packaging, it can also be expedient that the upper manifold seals with respect to the packaging and not with respect to a lower manifold. For example, the upper manifold can be brought into sealing engagement with a canister neck in such a way that the canister closure can be brought under the influence of vacuum. In the case of a flat packaging with a viewing window, the upper manifold can be brought into a sealing engagement with the packaging in a manner which surrounds the viewing window. It is important that a part of the closure or preferably the entire closure can be exposed to a vacuum, the upper manifold sealing with respect to the packaging and/or a lower manifold which can be part of the conveying device.

Although a perfect seal is advantageous, it is not necessary. A leak of the seal can thus certainly be tolerated, as long as it lies below a limit value which ensures a deformation of a leaky packaging, an escape of gas or material therefrom or a retardation of the vacuum generation which can be determined.

It is particularly expedient if the packaging stream is fed in on an endless conveyor and/or the sealing body circulates on an endless conveyor. Endless conveyors of this type are known in the prior art. They are robust and reliable.

The use of an endless conveyor as transport means for the packagings and/or an endless conveyor, on which the sealing body or sealing bodies are arranged, is particularly advantageous if the endless conveyor has an integrated energy channel which can be loaded with pneumatic energy which can be removed as vacuum for emptying gas from the sealing body. Endless conveyors of this type are known, for example, from WO 2008/104404 A2 and in the form of a particularly long-life and low-maintenance block chain from WO 2010/089101 A1. In endless conveyors of this type, pneumatic energy, in particular compressed air, but also optionally vacuum, is fed to an endlessly circulating toothed belt or an endlessly circulating block chain, for example at deflection rollers. The pneumatic energy is available in a channel which extends along the endless conveyor, in particular therein, and can be tapped off at any point. The sealing bodies can thus remove the pneumatic energy from the channel, in particular in a controlled manner, in order to generate a vacuum if a sealing body is moved together with a packaging. The vacuum is preferably generated from the compressed air in the channel via Venturi nozzles. Endless conveyors of this type also preferably had an energy line for electrical energy, with the result that electrically actuated elements and sensors can be supplied with electrical energy and, in addition, electrical signals such as measured values and control signals can be transmitted between a controller and/or evaluation unit and the sensors. The sealing bodies can also be connected to a unit or a plurality of units on the endless conveyor, which units cause an actuation and/or evaluation of the sensors and optionally an actuation of the vacuum generation means; however, this can also take place outside the endless conveyor in a central controller.

It is particularly advantageous if leaky packagings are retained on the endless conveyor and are rejected, in particular, during the return. The removal of leaky packagings from the packaging stream is therefore possible.

This can take place by way of electrically and/or pneumatically actuated grippers, suction bells or the like on the endless conveyor which has the sealing bodies, by the leaky packagings being picked up and therefore removed from the packaging stream and being rejected at a suitable point, expediently after the return. Instead, leaky packagings can also be pushed out laterally by means of corresponding ejection devices which can be provided instead of the grippers on the endless conveyor or in a stationary manner at a corresponding point after the inspecting section.

The packagings can also be retained on the endless conveyor, on which the packaging stream runs, by means of vacuum or grippers or the like, until they are situated around the deflection roller in the return, and can be ejected there, while the sealed packagings are ejected at a different point, or vice versa.

Furthermore, the invention provides a device for the vacuum-based continuous seal inspection of packagings which are fed in a continuous packaging stream, in particular foodstuff packagings, in which device a sealing body is provided which can be loaded with vacuum and can be moved together with a packaging along an inspecting section, and a sensor is provided for detecting a reaction to the loading of the packaging with vacuum and is coupled to an evaluation unit which can recognize that the packaging is sealed or leaky using the detected reaction.

The sensor can detect a deformation of the packaging, a pressure rise in the sealing body, a retarded vacuum formation in the sealing body, a gas in the sealing body and/or the like as a reaction to the loading with vacuum.

A mechanism for raising the packaging and/or a mechanism for lowering the sealing bodies can be provided.

The packagings can be arranged on a lower manifold, the sealing body sealing together with the lower manifold and the packaging being enclosed between the sealing body and the lower manifold.

An endless conveyor for feeding in the packaging stream can be provided and/or the sealing body can be fastened to an endless conveyor and can circulate with the latter.

The endless conveyor can have an integrated energy channel which can be loaded with pneumatic energy which can be removed as vacuum for emptying gas from the sealing body.

The endless conveyor can have a holding mechanism for the packagings, and a controller can be provided, by way of which leaky packagings are retained on the endless conveyor and are ejected during the return.

An optical sensor, a pressure sensor, a gas sensor, a throughflow sensor, a pressure switch and/or the like can be provided for detecting a reaction to the loading of the packaging with vacuum.

Furthermore, the invention provides the use of an endless conveyor with an energy supply line for pneumatic energy, as is known, for example, from WO 2010/089101 A1, for carrying out the method according to the invention or for the device according to the invention.

In summary, the invention is directed to a method for inspecting objects which are fed in a continuous stream, in particular packagings or components, characterized in that an inspecting body is moved together with an object along an inspecting section and a reaction to an inspection of the object is detected by means of a sensor, in order to determine whether the object satisfies a quality criterion, in particular is sealed or leaky or dimensionally accurate or functional. In one non-limiting configuration, the inspecting body includes the sensor. In another non-limiting configuration, the inspecting body causes an inspection of the object. In another non-limiting configuration, the inspecting body loads the object with a vacuum, a pressure and/or a mechanical, acoustic, optical, thermal and/or electrical or other test pulse and/or actuates, deflects, fills, empties, switches on and/or off, or stimulates in some other way the object or a part thereof. In another non-limiting configuration, an optical, acoustic, thermal, mechanical or other reaction of the object is detected by means of the sensor and is inspected with regard to a quality criterion. In another non-limiting configuration, the object is a packaging and the inspecting body is a sealing body, the sealing body being moved together with a packaging along the inspecting section, for the vacuum-based seal inspection of packagings which are fed in a continuous packaging stream, in particular foodstuff packagings, and being loaded with a vacuum and a reaction to the loading of the packaging with vacuum being detected by means of the sensor, in order to determine whether the packaging is sealed or leaky. In another non-limiting configuration, a deformation of the object, in particular a packaging or an injection molded component, a pressure rise in the inspecting body, a retarded vacuum formation in the inspecting body, a gas in the inspecting body, a noise in the inspecting body and/or an optical, thermal, acoustic and/or mechanically discernible reaction or the absence of a reaction of this type and/or the like are/is detected as a reaction to loading with vacuum. In another non-limiting configuration, the object is raised and/or the inspecting body is lowered and/or the inspecting body actuates an inspecting means. In another non-limiting configuration, the objects are arranged on a lower manifold, the sealing body seals together with the lower manifold, and the packaging is enclosed between the sealing body and the lower manifold. In another non-limiting configuration, the stream is fed on an endless conveyor and/or the inspecting body circulates on an endless conveyor. In another non-limiting configuration, the endless conveyor has an integrated energy channel which is loaded with pneumatic energy which is removed as vacuum for emptying gas from the inspecting body which is configured as a sealing body. In another non-limiting configuration, objects which do not satisfy the quality criterion, such as leaky packagings or components which are not dimensionally accurate, are retained on the endless conveyor and are ejected during the return. In another non-limiting configuration, a round inspecting device is used, in which a plurality of inspecting bodies circulate about an axis. In another non-limiting configuration, chambers or hoods which can be opened and/or closed optionally via a mechanism are used as inspecting bodies. In another non-limiting configuration, a line for energy, vacuum, pressure, data and/or a test pulse is guided radially to the inside and is fed by a central distributor. In another non-limiting configuration, the round inspecting device is arranged horizontally. In another non-limiting configuration, the round inspecting device is arranged perpendicularly or in an inclined manner with respect to the horizontal. In another non-limiting configuration, the inspecting body is configured as a sealing body with a flap and a lower plate, the flap falling onto the lower plate under the action of gravity and/or actuated by way of an actuator after the object is fed in, and opening under the action of gravity and/or actuated by way of an actuator before the object is dispensed. In another non-limiting configuration, the vacuum-based component inspection of components which are fed in a continuous component stream, in particular injection molded parts, characterized in that a sealing body is moved together with a component along an inspecting section and is loaded with vacuum and a reaction to the loading of the component with vacuum is detected by means of a sensor, in order to determine whether the component fulfills a quality requirement. In another non-limiting configuration, the vacuum-based seal inspection of packagings which are fed in a continuous packaging stream, in particular foodstuff packagings, characterized in that a sealing body is moved together with a packaging along an inspecting section and is loaded with vacuum and a reaction to the loading of the packaging with vacuum is detected by means of a sensor, in order to determine whether the packaging is sealed or leaky. In another non-limiting configuration, a deformation of the packaging, a pressure rise in the sealing body, a retarded vacuum formation in the sealing body, a gas in the sealing body and/or the like are/is detected as a reaction to loading with vacuum. In another non-limiting configuration, the packaging is raised and/or the sealing body is lowered. In another non-limiting configuration, the packagings are arranged on a lower manifold, the sealing body seals together with the lower manifold, and the packaging is enclosed between the sealing body and the lower manifold. In another non-limiting configuration, the packaging stream is fed in on an endless conveyor and/or the sealing body circulates on an endless conveyor. In another non-limiting configuration, the endless conveyor has an integrated energy channel which is loaded with pneumatic energy which is removed as vacuum for emptying gas from the sealing body. In another non-limiting configuration, leaky packagings) are retained on the endless conveyor and are ejected during the return. In another non-limiting configuration, there is provided a device for inspecting objects which are fed in a continuous stream, in particular packagings or components, characterized in that an inspecting body which can be moved together with an object along an inspecting section is provided, and a sensor for detecting a reaction to an inspection of the object is provided and can be coupled to an evaluation unit, in order to determine whether the object satisfies a quality criterion, in particular is sealed or leaky or dimensionally accurate or functional. In another non-limiting configuration, the inspecting body comprises the sensor. In another non-limiting configuration, the inspecting body is configured for carrying out an inspection of the object. In another non-limiting configuration, the inspecting body can load the object with a vacuum, a pressure and/or a mechanical, acoustic, optical, thermal and/or electrical or other test pulse and/or can actuate, deflect, fill, empty, switch on and/or off, or stimulate in some other way the object or a part thereof. In another non-limiting configuration, the sensor is configured for detecting an optical, acoustic, thermal, mechanical or other reaction of the object, for the inspection with regard to a quality criterion. In another non-limiting configuration, the object is a packaging and the inspecting body is a sealing body, it being possible for the sealing body to be moved together with a packaging along the inspecting section, for the vacuum-based seal inspection of packagings which are fed in a continuous packaging stream, in particular foodstuff packagings, and to be loaded with vacuum, and for a reaction to the loading of the packaging with vacuum to be detected by means of the sensor and to be evaluated by means of the evaluation unit, in order to determine whether the packaging is sealed or leaky. In another non-limiting configuration, the sensor and/or the evaluation unit are/is configured for detecting, as a reaction to loading with vacuum, a deformation of the object, in particular a packaging or an injection molded component, a pressure rise in the inspecting body, a retarded vacuum formation in the inspecting body, a gas in the inspecting body, a noise in the inspecting body and/or an optical, thermal, acoustic and/or mechanically discernible reaction or an absence of a reaction of this type and/or the like. In another non-limiting configuration, means for raising the object are raised and/or for lowering the inspecting body are provided and/or the inspecting body has an inspecting means. In another non-limiting configuration, the objects are arranged on a lower manifold, the sealing body seals together with the lower manifold, and the packaging is enclosed between the sealing body and the lower manifold. In another non-limiting configuration, the stream is fed in on an endless conveyor and/or the inspecting body circulates on an endless conveyor. In another non-limiting configuration, the endless conveyor has an integrated energy channel which is loaded with pneumatic energy which is removed as vacuum for emptying gas from the inspecting body which is configured as a sealing body. In another non-limiting configuration, objects which do not satisfy the quality criterion, such as leaky packagings or components which are not dimensionally accurate, are retained on the endless conveyor and are ejected during the return. In another non-limiting configuration, a round inspecting device is provided, in which a plurality of inspecting bodies circulate about an axis. In another non-limiting configuration, the inspecting bodies have chambers or hoods which can be opened and/or closed via a mechanism. In another non-limiting configuration, a line for energy, vacuum, pressure, data and/or a test pulse is guided radially to the inside and is coupled to a central distributor. In another non-limiting configuration, the round inspecting device is arranged horizontally or substantially horizontally. In another non-limiting configuration, the round inspecting device is arranged perpendicularly or in an inclined manner with respect to the horizontal. In another non-limiting configuration, the inspecting body is configured as a sealing body with a flap and a lower plate, the flap falling onto the lower plate under the action of gravity and/or actuated by way of an actuator after the object is fed in, and opening under the action of gravity and/or actuated by way of an actuator before the object is dispensed. In another non-limiting configuration, the continuous vacuum-based inspection of components which are fed in a continuous stream, in particular injection molded parts, characterized in that a sealing body is provided which can be loaded with vacuum and can be moved together with a component along an inspecting section, and a sensor for detecting a reaction to the loading of the component with vacuum is provided and is coupled to an evaluation unit which can recognize that the component is dimensionally accurate or not dimensionally accurate or the like using the detected reaction. In another non-limiting configuration, the vacuum-based continuous seal inspection of packagings which are fed in a continuous packaging stream, in particular foodstuff packagings, characterized in that a sealing body is provided which can be loaded with vacuum and can be moved together with a packaging along an inspecting section, and a sensor for detecting a reaction to the loading of the packaging with vacuum is provided and is coupled to an evaluation unit which can recognize that the packaging is sealed or leaky using the detected reaction. In another non-limiting configuration, the sensor can detect a deformation of the packaging, a pressure rise in the sealing body, a retarded vacuum formation in the sealing body, a gas in the sealing body and/or the like as a reaction to the loading with vacuum. In another non-limiting configuration, a mechanism for raising the packaging and/or a mechanism for lowering the sealing bodies are/is provided. In another non-limiting configuration, the packagings are arranged on a lower manifold, the sealing body seals together with the lower manifold, and the packaging is enclosed between the sealing body and the lower manifold. In another non-limiting configuration, an endless conveyor for feeding in the packaging stream is provided and/or the sealing body is fastened to an endless conveyor and circulates with the latter. In another non-limiting configuration, the endless conveyor has an integrated energy channel which can be loaded with pneumatic energy which can be removed as vacuum for emptying gas from the sealing body. In another non-limiting configuration, the endless conveyor has a holding mechanism for the packagings and a controller is provided, by way of which leaky packagings are retained on the endless conveyor and are ejected during the return. In another non-limiting configuration, an optical sensor, a pressure sensor, a gas sensor, a throughflow sensor, a pressure switch and/or the like are/is provided for detecting a reaction to the loading of the packaging with vacuum.

Further refinements can be gathered, in particular, from the independent claims and are in each case independently inventive.

Further refinements, properties and details of the invention can be gathered from the following description and figures, and from the claims.

Figure 1:
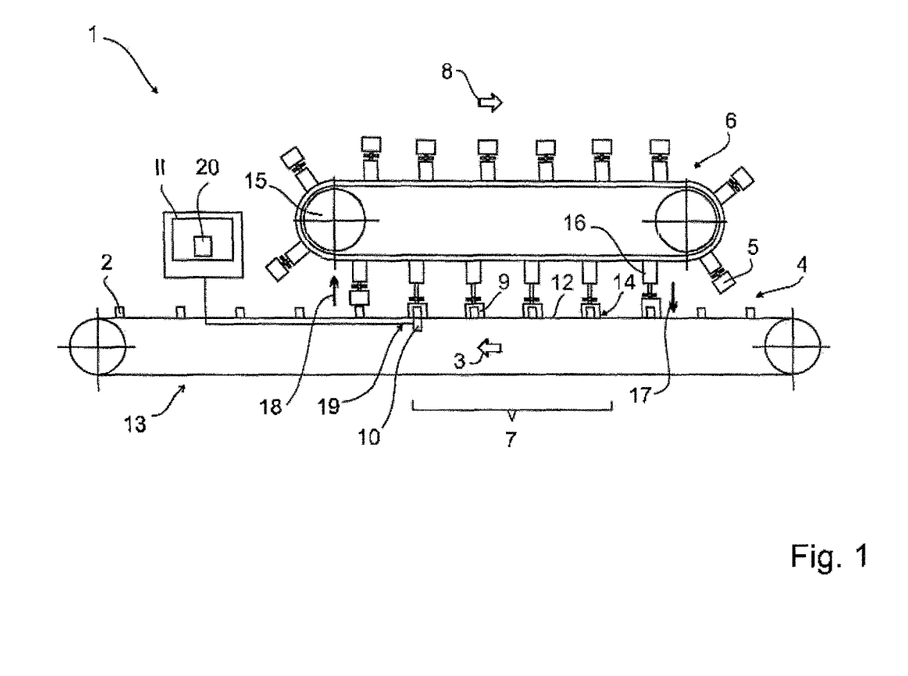
FIG. 1 illustrates a device for the vacuum-based continuous seal inspection of packagings which are fed in a continuous packaging stream.

The device 1 which is shown in FIG. 1 for the vacuum-based continuous seal inspection of packagings 2 which are moved continuously in a packaging stream 4 which runs along an arrow 3 comprises sealing bodies 5 which run synchronously with the packaging stream 4 in the direction of an arrow 8 along an inspecting section 7, by way of example on an endless conveyor 6 and load the packagings with a vacuum 9, a sensor 10 for detecting a reaction to the loading of a packaging 2 with vacuum being provided and being coupled to an evaluation unit 11 which can recognize that the packaging 2 is sealed or leaky using the detected reaction.

The packaging stream 4 supplies packagings behind one another and optionally also next to one another, in this case on a conveying face 12 of an endless conveyor 13, which packagings have been filled in the preceding processing step with products such as foodstuffs and have been closed in an air-tight manner, for example welded with transparent material. The packaging stream 4 is continuous, that is to say it moves in the direction of the arrow 3 at a preferably constant speed which, however, can possibly change, and it also being possible for standstill times to be provided, in particular in a cyclical manner. It is important that the sealing bodies 5 which can be configured, for example, as suction bells which are, in particular, transparent are moved synchronously with respect to the packagings 2 at least in the region of the inspecting section 7, that is to say if required likewise at a variable speed or with standstill times.

During the synchronous running along the inspecting section 7, the sealing bodies 5 are lowered in the example which is shown, in order to seal together with a lower manifold 14 which can be of separate configuration or, as shown, can be the surface 12.

The vacuum 9 is then preferably generated; the sealing bodies 5, however, optionally already generate a vacuum briefly before or in an uninterrupted manner. The energy for this purpose can come from the endless conveyor 6 which is preferably configured with a channel which extends along its longitudinal direction in an endless manner or along sections in the endless conveyor 6 and can be loaded, for example, with compressed air. The compressed air is preferably fed in axially at a deflection point 15 and is fed radially to the channel in the region of the support between the deflection point 15 and the endless conveyor 6, as is known for endless conveyors 6 of this type. The vacuum 9 is generated from the compressed air, for example, via Venturi nozzles. The compressed air can also cause the lowering and raising mechanisms 16 to lower along the arrow 17 at the beginning of the inspecting section 7 and to raise up along the arrow 18 at the end of the inspecting section 7, which expediently takes place in a valve-controlled manner.

Here, the device 1 which is shown comprises precisely one measurement point 19 which is stationary here and at which the sensor 10 and optionally further sensors detects or detect the reaction to the loading with vacuum. However, the measurement point does not have to be stationary and a plurality of measurement points can be provided. By way of example, an optical sensor 10 is illustrated, by way of which a deformation of the packaging 2 can be detected at the measurement point 19, which is illustrated by the image 20 in the evaluation unit 11. An acoustic sensor can optionally detect the development of noise, or a pressure sensor can detect the pressure drop in the sealing body as a result of the escape of air or gas from a leaky packaging, etc. The evaluation unit 11 is expediently a correspondingly configured computer unit. The sensor 10 can also be a pressure sensor, etc., and a plurality of, in particular different, sensors can be provided at the measurement point 19. Instead of the stationary sensor 10 or in addition, one sensor or a plurality of sensors can be provided on or in the sealing bodies 5. Said sensors can be coupled to the evaluation unit 11 via an electric energy line in the endless conveyor 6 and taps at the deflection roller 15 and/or by radio.

The evaluation unit 11 then detects using the sensor data whether a packaging 2 is sealed or leaky. An ejection of leaky packagings 2 from the packaging stream 4 can be brought about. In other applications, the sensor can detect, for example, whether a component to be inspected is moving as desired, or whether an LED assembly which is to be inspected outputs light, or whether a fire alarm reacts acoustically and/or optically to smoke which is to be allowed into the sealing body, or the like; the sensor and/or the actuator for the inspection with regard to a quality criterion of this type can be arranged on, inside and/or outside the inspecting body which does not have to be a sealing body, depending on the inspection to be carried out.

Figure 2:
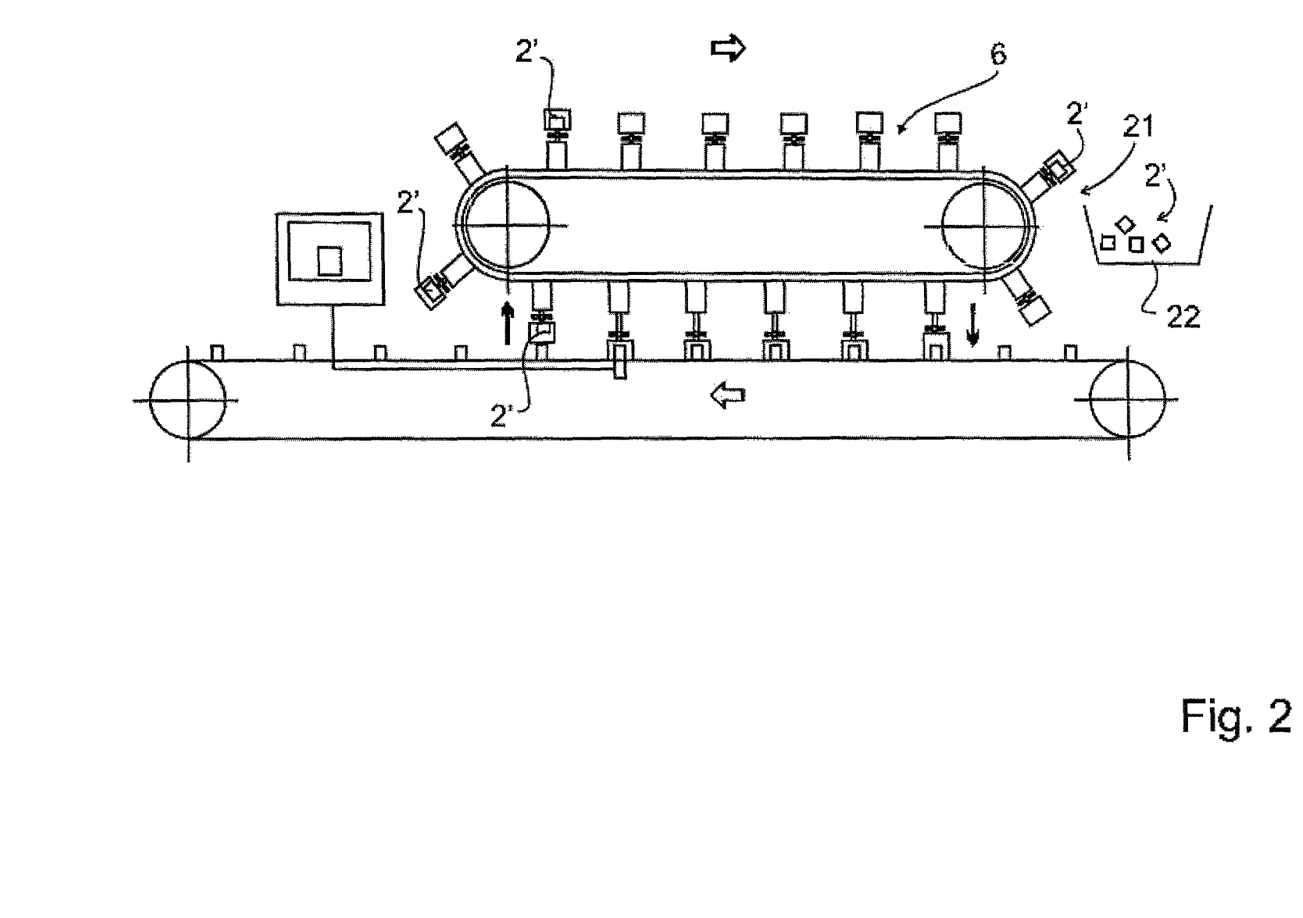
FIG. 2 illustrates a further embodiment of a device according to the invention.

The ejection can take place (cf. FIG. 2) by way of driving of a leaky packaging 2' on the endless conveyor 6 as far as an ejection point 21 into a container 22 or the like. To this end, suction bells or grippers or the like which can pick up and drop leaky packagings 2' can be provided on the endless conveyor 6 at corresponding points, in the sealing bodies 5 shown here by way of example.

Figure 3:
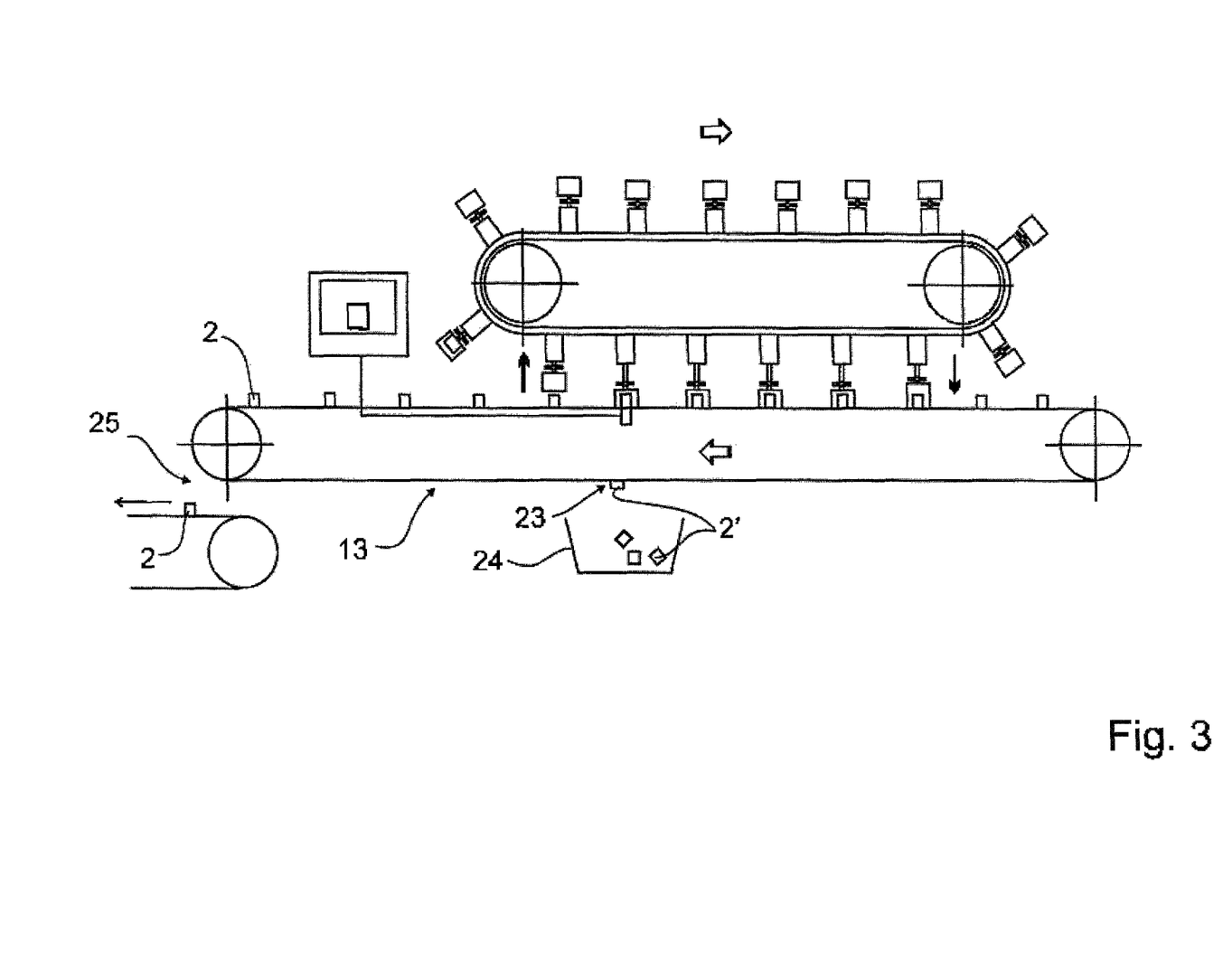
FIG. 3 illustrates a further embodiment of a device according to the invention.

In the refinement which is shown in FIG. 3, leaky packagings 2' are retained on the endless conveyor 13 until an ejection point 23, where they fall into a container 24, whereas sealed packagings are processed further at a different point 25, for example are fed to a conveying device 26.

Figure 4:
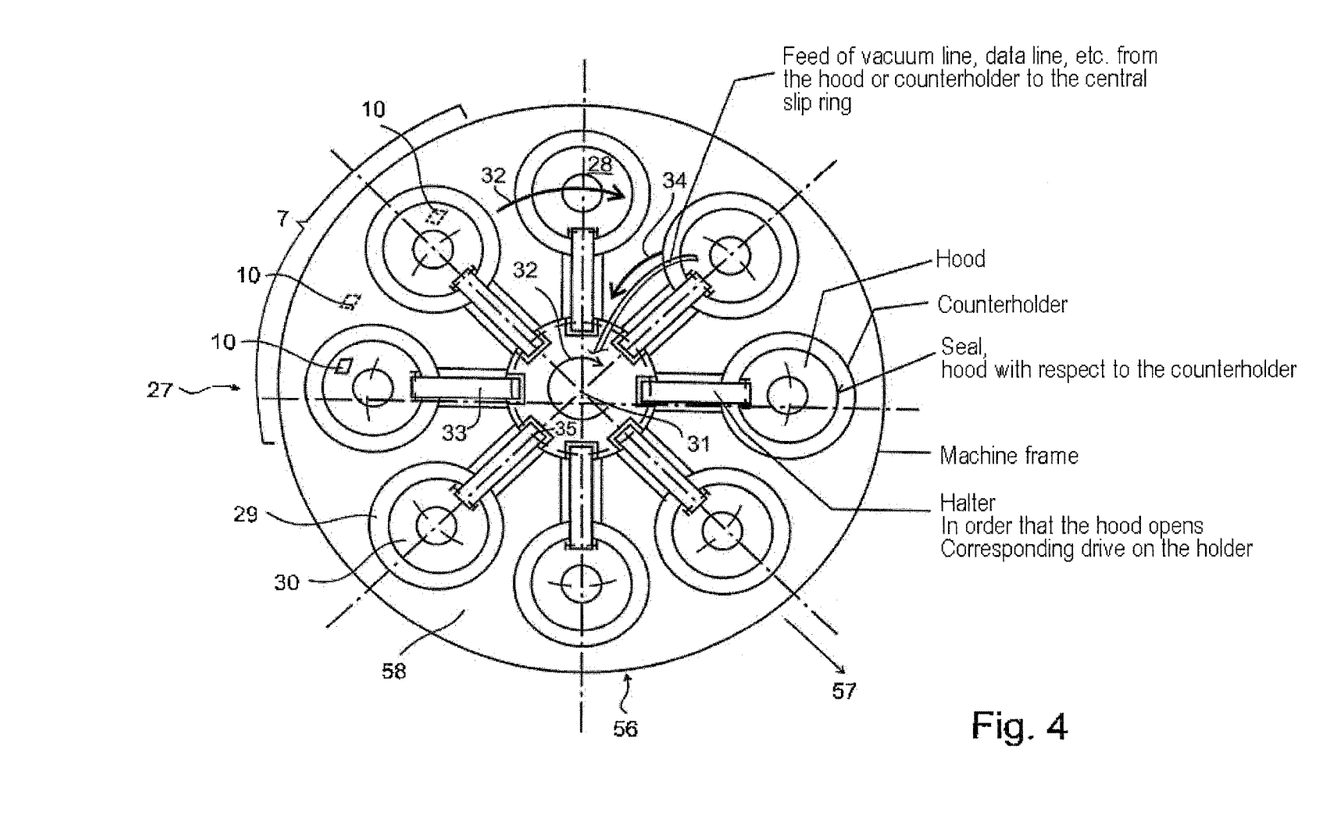
FIG. 4 illustrates an embodiment with a round table.

In the embodiment which is shown in FIG. 4, a round inspecting device, in the form of a round table 27 here, is provided, in which a plurality of inspecting bodies, in the form of chambers 28 here which are formed from hoods 30 which close on counterholders 29, circulate around an axis 31 in the manner of a carousel, for example along the arrows 32.

Each of the chambers 28 can be opened and/or closed, in particular automatically, via a mechanism 33 (lever, pneumatic drive, electric drive, etc.).

It is particularly advantageous that the opening and closing of the chambers 28 is arbitrary, as long as a separately controllable or actuable mechanism 33 is provided for each chamber 28.

Each hood 30 is sealed in the closed state via a seal with respect to the counterholder 29 which is running together with it and thus forms an autonomous volume for the measurement operation. Lines 34, of which only one is shown for the sake of simplification, for energy, vacuum, pressure, data and/or a test pulse are guided radially on the inside and are fed by a central distributor 35, for example a slip ring or a vacuum distributor or the like, as are known from WO 2008/104404 A2 or WO 2010/089101 A1, in order to feed energy into a chain.

The loading means with objects and also the removal means can be arranged where desired, for example at the arrows 56, 57, since the opening and closing of the chambers 28 is brought about by a separate drive. As a result, this embodiment is particularly flexible. The inspecting section 7 extends between the loading means 56 and the removal means 57, and at least one sensor 10 can be arranged on the machine frame 58 and/or on and/or in the hoods 30 and/or counterholders 29.

The embodiment of FIG. 4 is particularly suitable for a vacuum-based seal inspection of beakers and large-volume packaging units, such as milk cartons. It is preferably arranged horizontally.

Figure 5:
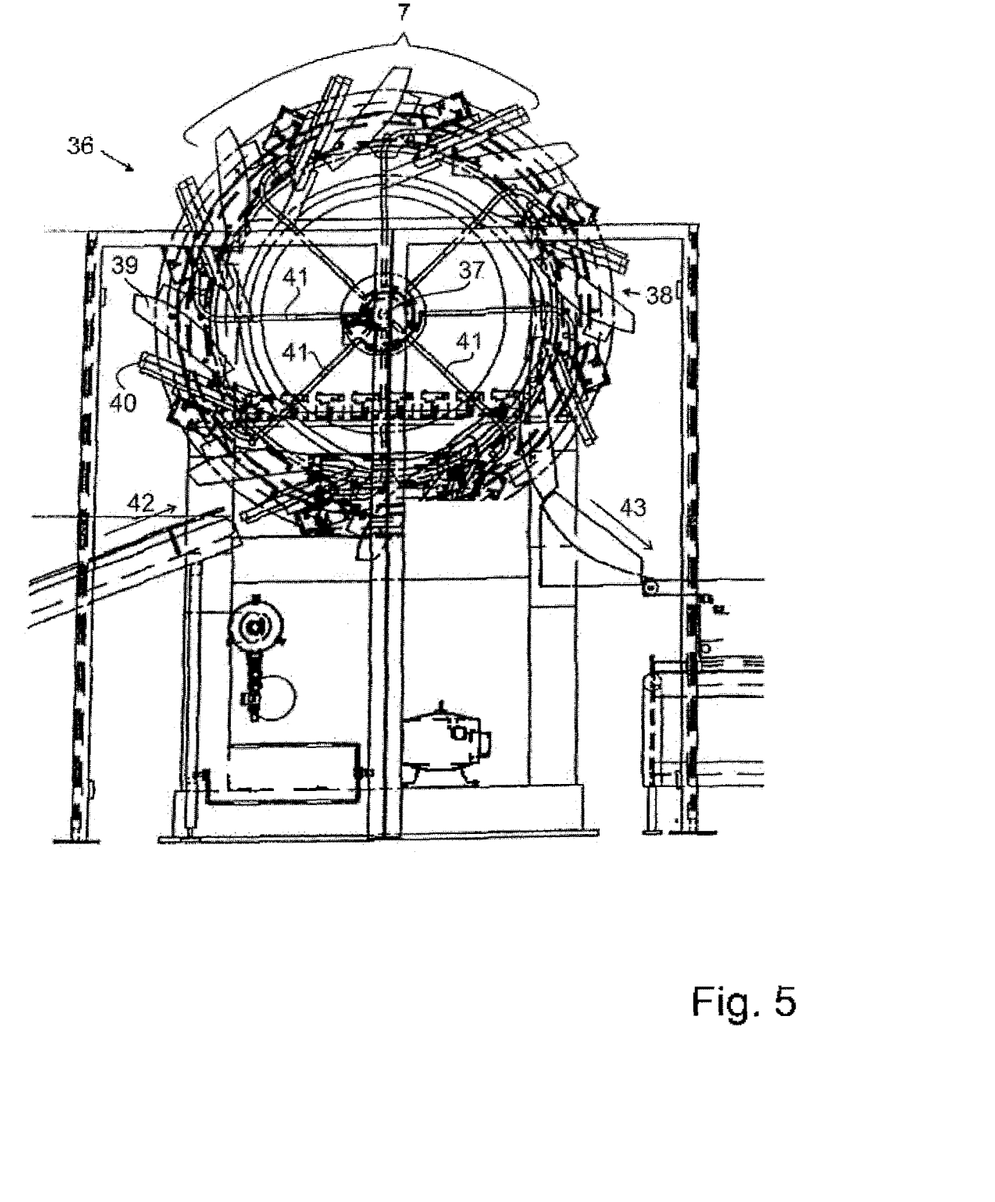
FIGS. 5 and 6 illustrate an embodiment which is similar to a paddle wheel.
Figure 6:
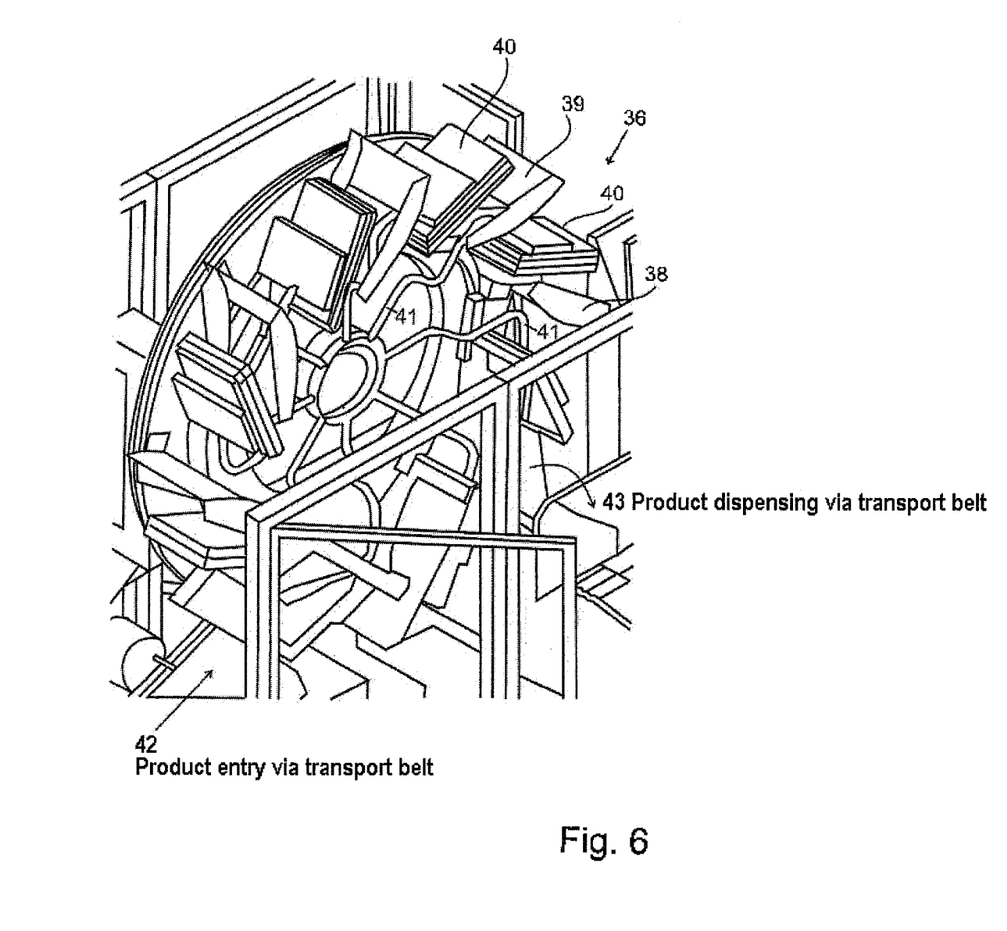

The embodiment according to FIGS. 5 and 6 has a round inspecting device 35 which is faintly reminiscent of a paddle wheel and is preferably arranged perpendicularly or in a manner which is inclined with respect to the horizontal, but also optionally horizontally. A wheel rotates about a central axis 37 and, on the external diameter, has chambers 38 which comprise or form inspecting bodies. During the rotational operation, one flap 39 falls onto a lower manifold 40 per individual chamber and seals it with respect to the outside, possibly assisted by way of an actuating mechanism. The sealing action preferably takes place by way of seals on the respective cell. The individual chambers have sensors 10 and/or are guided past at least one sensor 10 along the inspecting section 7.

Lines 41 for vacuum, pressure, electrical or other energy, electrical or other signals are guided to the inside toward the central axis 37 and, in a similar manner to the refinement according to FIG. 3, are fed or guided further via a slip ring or a rotary leadthrough or the like.

In contrast to the embodiment according to FIG. 3, the loading and removal take place at points 42, 43 which are provided for this purpose in the system and not at any desired point. For removal, the respective flap 39 can be opened in a manner induced by gravity and/or by way of actuation, for example by way of a finger which is positioned at a suitable point and raises up the flap.

The embodiment according to FIGS. 5 and 6 is particularly suitable for seal inspection of chip bags, saltines and the like.

Figure 7:
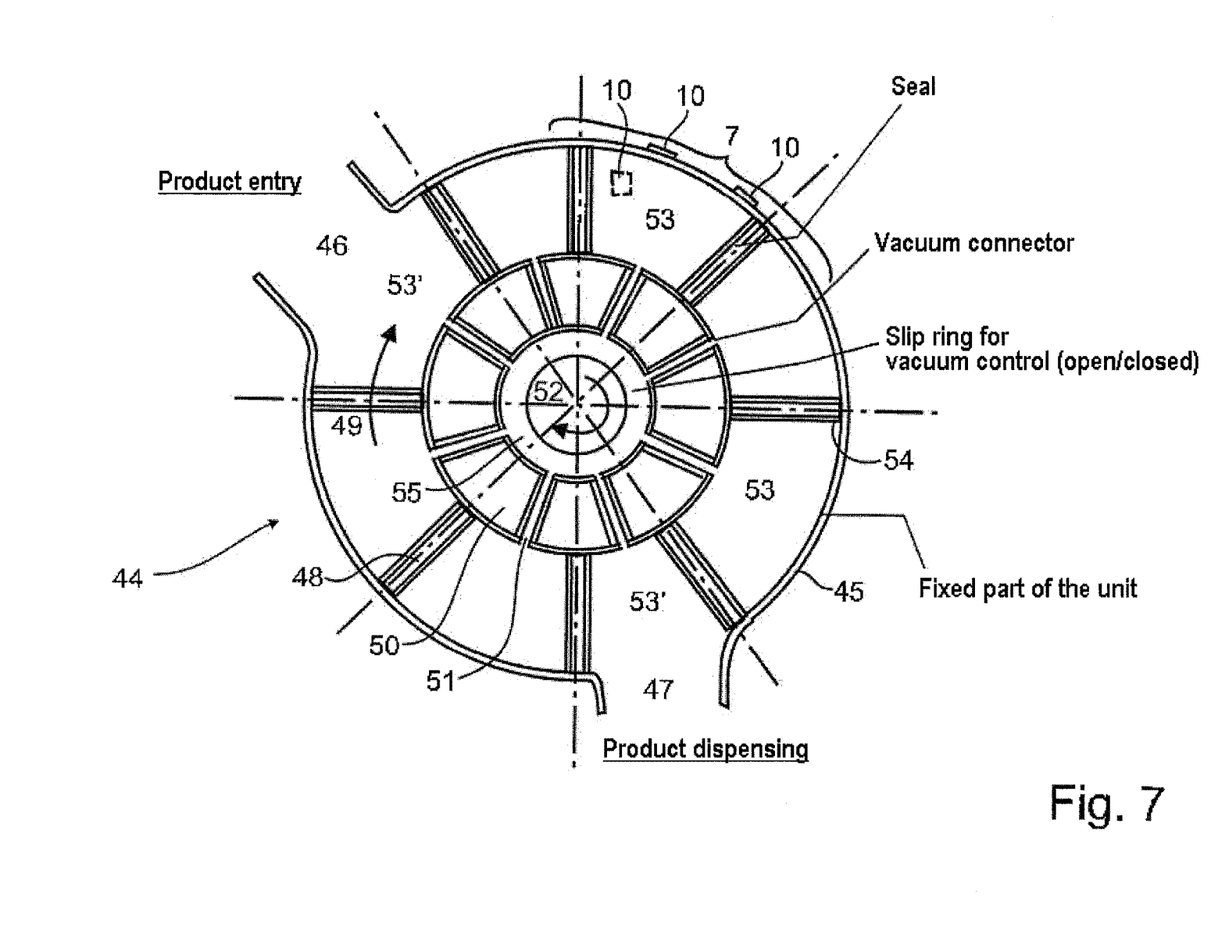
FIG. 7 illustrates a further embodiment.

The device 44 of FIG. 7 has an outer boundary 45 with a feed opening 46 and a dispensing opening 47 for continuously fed and dispensed objects, respectively. A rotor 50 with lamellae 48 circulates, for example, along the arrow 49. The rotor 50 has channels 51, through which vacuum which is fed in centrally via a vacuum feed 52 passes into inspecting bodies or chambers 53 which are formed by the lamellae 48. The lamellae 48 are expediently sealed via a seal 54 with respect to the boundary 45, and a slip ring 55 can be provided in the interior for controlling the vacuum output; for example, it is not necessary to generate vacuum in the chamber 53' which is open in each case to the feed opening 46 (or dispensing opening 47).

One or more sensors 10 can be arranged along the inspecting section 7.

This refinement can be used particularly advantageously for the vacuum-based seal inspection of tubular bag packagings, for example chip bags, saltines, etc.

The invention claimed is:

1. A method for inspecting objects in the form of packagings or components which are fed in a continuous stream and along a movement axis, characterized in that there is provided a plurality of inspecting bodies wherein each of said inspecting bodies is moved together with each of said objects along an inspecting section and a reaction to an inspection of the object is detected by means of a sensor in order to determine whether the object satisfies one or more quality criterion selected from the group consisting of a sealed object, a leaky object, a dimensionally accurate object, and a functional object, each of said inspecting bodies connected to a device conveying arrangement that is configured to move each of said inspecting bodies, said device conveying arrangement lying in an axis parallel to said movement axis prior to, during and after said inspection of said objects, each of said inspecting bodies connected to a movement arrangement that is configured to move each of said inspecting bodies relative to said object prior to and after said inspection of said object by said inspecting body and to move each of said inspecting bodies with said object during said inspection of said object by said inspecting body, and separating each of said objects that fail said inspection from said objects that pass said inspection.

2. The method as claimed in claim 1, characterized in that the inspecting body comprises the sensor.

3. The method as claimed in claim 1, characterized in that the inspecting body loads the object with a vacuum, a pressure and/or a mechanical, acoustic, optical, thermal and/or electrical or other test pulse and/or actuates, deflects, fills, empties, switches on and/or off, or stimulates in some other way the object or a part thereof.

4. The method as claimed in claim 1, characterized in that an optical, acoustic, thermal, mechanical or other reaction of the object is detected by means of the sensor and is inspected with regard to a quality criterion.

5. The method as claimed in claim 1, characterized in that the object is in a form of said packaging and the inspecting body is a sealing body, the sealing body being moved together with said packaging along the inspecting section used for a vacuum-based seal inspection of said packaging, a vacuum seal of said packaging being detected by means of the sensor in order to determine whether the packaging is sealed or leaky.

6. The method as claimed in claim 1, characterized in that a deformation of the object in the form of said packaging or said component in the form of an injection molded component are tested to determine is said packaging or said component are dimensionally correct by one or more tests selected from the group consisting of a test for testing a pressure rise in the object, a test for testing a retarded vacuum formation in the object, a test for testing a gas in the object, a test for testing a noise in the object, an optical test, a thermal test, an acoustic test, and a mechanical test.

7. The method as claimed in claim 1, characterized in that the object is raised and/or the inspecting body is lowered and/or the inspecting body actuates an inspecting means.

8. The method as claimed in claim 1, characterized in that the objects are arranged on a lower manifold, the sealing body seals together with the lower manifold, and the packaging is enclosed between the sealing body and the lower manifold.

9. The method as claimed in claim 1, characterized in that the stream is fed on an endless conveyor and/or the inspecting body circulates on an endless conveyor.

10. The method as claimed in claim 1, characterized in that the endless conveyor has an integrated energy channel which is loaded with pneumatic energy which is removed as vacuum for emptying gas from the inspecting body which is configured as a sealing body.

11. The method as claimed in claim 9, characterized in that objects which do not satisfy the quality criterion which are not dimensionally accurate are retained on the endless conveyor and are ejected during the return.

12. The method as claimed in claim 1, characterized in that a round inspecting device is used, in which a plurality of inspecting bodies circulate about an axis.

13. The method as claimed in claim 12, characterized in that chambers or hoods which can be opened and/or closed optionally via a mechanism are used as inspecting bodies.

14. The method as claimed in claim 12, characterized in that a line for energy, vacuum, pressure, data and/or a test pulse is guided radially to the inside and is fed by a central distributor.

15. The method as claimed in claim 12, characterized in that the round inspecting device is arranged horizontally.

16. A method as defined in claim 1, for the vacuum-based component inspection of components in the form of molded parts which are fed in a continuous component stream, characterized in that a sealing body is moved together with said component along said inspecting section and is loaded with vacuum and a reaction to the loading of the component with vacuum is detected by means of a sensor in order to determine whether the component fulfills one or more of said quality criterion.

17. A method as defined in claim 1, for the vacuum-based seal inspection of packagings in the form of foodstuff packaging which are fed in a continuous packaging stream, characterized in that a sealing body is moved together with said packaging along said inspecting section and is loaded with vacuum and a reaction to the loading of the packaging with vacuum is detected by means of a sensor; in order to determine whether the packaging is sealed or leaky.

18. The method as claimed in claim 17, characterized in that a deformation of the packaging, a pressure rise in the sealing body, a retarded vacuum formation in the sealing body, and/or a gas in the sealing body is detected as a reaction to loading with vacuum.

19. The method as claimed in claim 18, characterized in that the packaging is raised and/or the sealing body is lowered.

20. The method as claimed in claim 18, characterized in that the packagings are arranged on a lower manifold, the sealing body seals together with the lower manifold, and the packaging is enclosed between the sealing body and the lower manifold.

21. The method as claimed in claim 18, characterized in that the packaging stream is fed in on an endless conveyor and/or the sealing body circulates on an endless conveyor.

22. The method as claimed in claim 18, characterized in that the endless conveyor has an integrated energy channel which is loaded with pneumatic energy which is removed as vacuum for emptying gas from the sealing body.

23. The method as claimed in claim 18, characterized in that leaky packagings are retained on the endless conveyor and are ejected during the return.

24. A device for inspecting objects which are fed in a continuous stream, characterized in that there is provided a plurality of inspecting bodies wherein each of said inspecting bodies can be moved together with each of said objects along an inspecting section, and a sensor for detecting a reaction to an inspection of the object is provided and can be coupled to an evaluation unit in order to determine whether the object satisfies one or more quality criterion selected from the group consisting of a sealed object, a leaky object, a dimensionally accurate object, and a functional object, each of said inspecting bodies connected to a device conveying arrangement that is configured to move each of said inspecting bodies, said device conveying arrangement lying in an axis parallel to said movement axis prior to, during and after said inspection of said objects, each of said inspecting bodies connected to a movement arrangement that is configured to move each of said inspecting bodies relative to said object prior to and after said inspection of said object by said inspecting body and to move each of said inspecting bodies with said object during said inspection of said object by said inspecting body, and separating each of said objects that fail said inspection from said objects that pass said inspection.

25. A method for inspecting a plurality of objects which are fed in a continuous stream comprising:
providing a conveying arrangement configured to move each of said objects in said continuous stream;
feeding each of said objects to said conveying arrangement to be moved along said conveying arrangement in said continuous stream;
providing an inspection arrangement configured to test a quality criteria of each of said objects as said objects are moved in continuous stream on said conveying arrangement, said inspection arrangement position only partially along said conveying arrangement, said inspection arrangement including a plurality of inspection devices, each of said inspection devices configured to move along said conveying arrangement as each of said objects are moved along said conveying arrangement in said continuous stream, each of said inspection devices connected to a device conveying arrangement that is configured to move each of said inspection devices along said conveying arrangement as each of said objects are moved along said conveying arrangement in said continuous stream, each of said inspection devices connected to a movement arrangement that is configured to move each of said inspection devices relative to said device conveying arrangement prior to and after said inspection of said object by said inspection device and to move each of said inspection devices with said object during said inspection of said object by said inspection device, each of said inspection devices configured to test at least one of said objects, said quality criteria including one or more criteria selected from the group consisting of an air-tight seal, a liquid-tight seal, dimensional requirement of each of said objects, and a functional requirement of each of said objects, said inspection arrangement including a sensor;

moving each of said inspection devices of said inspection arrangement along at least one of said objects as each of said objects moves along said conveyor arrangement in said continuous stream;

inspecting each of said objects by said inspection arrangement as said objects remain on said conveyor arrangement and move along said conveying arrangement in said continuous stream; and, separating each of said objects that fail said inspection during said step of inspecting from said objects that pass said inspection during said step of inspecting.

26. The method as defined in claim 25, wherein said step of separating includes removing each of said objects from said conveyor arrangement that fail said inspection from said conveyor arrangement as said objects move in said continuous stream, said inspection arrangement is configured to move each of said objects off of said conveyor arrangement that fail said inspection and to later deposit said objects that have been moved off of said conveyor arrangement into a rejection arrangement that is spaced from said conveyor arrangement.

27. The method as defined in claim 26, wherein said said inspection arrangement is configured to lift each of said objects off of said conveyor arrangement that fail said inspection.

28. The method as defined in claim 25, wherein conveyor arrangement includes an endless conveyor, said objects are continuously moved along said endless conveyor as said objects are moved toward said inspection arrangement and during said inspection of each of said objects by said inspection arrangement, said objects are maintain at a generally constant distance from one another on said endless conveyor as said objects are moved toward said inspection arrangement and during said inspection of each of said objects by said inspection arrangement.

29. The method as defined in claim 26, wherein conveyor arrangement includes an endless conveyor that lies in a conveyor axis, said objects are continuously moved along said endless conveyor as said objects are moved toward said inspection arrangement and during said inspection of each of said objects by said inspection arrangement, said objects are maintain at a generally constant distance from one another on said endless conveyor as said objects are moved toward said inspection arrangement and during said inspection of each of said objects by said inspection arrangement.

30. The method as defined in claim 27, wherein conveyor arrangement includes an endless conveyor that lies in a conveyor axis, said objects are continuously moved along said endless conveyor as said objects are moved toward said inspection arrangement and during said inspection of each of said objects by said inspection arrangement, said objects are maintain at a generally constant distance from one another on said endless conveyor as said objects are moved toward said inspection arrangement and during said inspection of each of said objects by said inspection arrangement.

31. The method as defined in claim 28, wherein an axis of movement of said device conveying arrangement is parallel to said conveyor axis prior to, during and after said inspection of said objects.

32. The method as defined in claim 29, wherein an axis of movement of said device conveying arrangement is parallel to said conveyor axis prior to, during and after said inspection of said objects.

33. The method as defined in claim 30, wherein an axis of movement of said device conveying arrangement is parallel to said conveyor axis prior to, during and after said inspection of said objects.

34. The method as defined in claim 25, wherein each of said inspection devices of said inspection arrangement applies a vacuum to each of said objects during said inspection of each of said objects, said inspection arrangement configured to detect a deformation of said objects, a pressure rise in said inspection device, a retarded vacuum formation in said inspection device, a gas in said inspection device, or combinations thereof during said inspection of each of said objects.

35. The method as defined in claim 34, wherein said conveyor arrangement includes a sealing manifold that is configured to receive each of said objects when said objects are fed onto said conveyor arrangement, said sealing manifold configured to form a gas seal with at least one of said inspection devices while said at least one inspection device is performing said inspection of said at least one objects.

36. The method as defined in claim 26, wherein each of said inspection devices of said inspection arrangement applies a vacuum to each of said objects during said inspection of each of said objects, said inspection arrangement configured to detect a deformation of said objects, a pressure rise in said inspection device, a retarded vacuum formation in said inspection device, a gas in said inspection device, or combinations thereof during said inspection of each of said objects.

37. The method as defined in claim 36, wherein said conveyor arrangement includes a sealing manifold that is configured to receive each of said objects when said objects are fed onto said conveyor arrangement, said sealing manifold configured to form a gas seal with at least one of said inspection devices while said at least one inspection device is performing said inspection of said at least one objects.

38. The method as defined in claim 33, wherein each of said inspection devices of said inspection arrangement applies a vacuum to each of said objects during said inspection of each of said objects, said inspection arrangement configured to detect a deformation of said objects, a pressure rise in said inspection device, a retarded vacuum formation in said inspection device, a gas in said inspection device, or combinations thereof during said inspection of each of said objects.

39. The method as defined in claim 38, wherein said conveyor arrangement includes a sealing manifold that is configured to receive each of said objects when said objects are fed onto said conveyor arrangement, said sealing manifold configured to form a gas seal with at least one of said inspection devices while said at least one inspection device is performing said inspection of said at least one objects.

40. The method as defined in claim 25, wherein said object is in the form of packaging, said packaging has an item sealed in said packaging.

41. The method as defined in claim 39, wherein said object is in the form of packaging, said packaging has an item sealed in said packaging.

* * * * *